United States Patent [19]

Koch et al.

[11] Patent Number: 4,475,821
[45] Date of Patent: Oct. 9, 1984

[54] MIXING CHAMBER

[75] Inventors: Dieter Koch; Wolfgang Risler, both of Weyhe, Fed. Rep. of Germany

[73] Assignee: Bruker-Analytische Messtechnik GmbH, Rheinstetten-Forchheim, Fed. Rep. of Germany

[21] Appl. No.: 306,757

[22] Filed: Sep. 29, 1981

[30] Foreign Application Priority Data

Oct. 7, 1980 [DE] Fed. Rep. of Germany ....... 3037898

[51] Int. Cl.³ .............................................. B01F 5/06
[52] U.S. Cl. .................................... 366/160; 366/340; 422/133; 138/38
[58] Field of Search ...................... 366/340, 336–337, 366/160; 422/133; 138/38, 42

[56] References Cited

U.S. PATENT DOCUMENTS

| 2,297,817 | 10/1942 | Truxell et al. | 138/42 |
| 2,424,932 | 7/1947 | Juhasz | 259/44 X |
| 2,815,532 | 10/1957 | Braunlich | 366/336 |
| 3,208,958 | 9/1965 | Jennings | 422/133 |
| 3,665,965 | 5/1972 | Baumann | 138/42 |
| 3,905,395 | 9/1975 | Hupe | 366/341 |
| 4,162,689 | 7/1979 | Zdrodowski | 137/624.12 |
| 4,213,936 | 7/1980 | Lodrick | 422/133 |
| 4,329,067 | 5/1982 | Goudy, Jr. | 366/182 |

FOREIGN PATENT DOCUMENTS

| 2263769 | 2/1974 | Fed. Rep. of Germany . |
| 2803771 | 2/1979 | Fed. Rep. of Germany . |
| 137406 | 5/1979 | German Democratic Rep. . |
| 350716 | 6/1931 | United Kingdom ................ 366/340 |

Primary Examiner—Stephen Marcus
Assistant Examiner—Brian J. Bowman
Attorney, Agent, or Firm—Burmeister, York, Palmatier, Hamby & Jones

[57] ABSTRACT

A mixing chamber for liquids, which are supplied to the mixing chamber in measured quantities one after the other alternating over a period of time, in particular for liquid chromatographs is divided by a fine-pored filter plate (109) into two areas (105, 106). The inlet pipe (111) is connected to one area and the outlet pipe (112) is connected to the other of these areas. The two areas (105, 106) each widen out in a conical shape from the opening of the connected pipe (111) towards the filter plate (109). The filter plate (109) preferably consists of a steel or glass frit with a pore size in the range of 2 to 50 μm.

10 Claims, 4 Drawing Figures

POROUS CIRCULAR FILTER PLATE OF SINTERED MATERIAL. PORE SIZE: 2-50 MICRONS.

MIXING CHAMBER

FIELD OF THE INVENTION

The invention relates to a mixing chamber for liquids, which are supplied to the mixing chamber in measured quantities one after the other alternating over a period of time, in particular for liquid chromatographs.

BACKGROUND OF THE INVENTION

In liquid chromatographs, one frequently works with liquid mixtures whereof the mixing proportion is varied as a function of time in a definite manner. On account of the very low conveying capacities and the very varied viscosities of the liquids to be analysed, definite mixing proportions cannot be achieved due to the fact that the streams of the liquids to be mixed are supplied together at the same time and the mixing proportion is determined by regulating the force of the stream. Instead of this, small portions of the liquids to be mixed together are supplied continuously in succession to a mixing chamber by means of valves having a time control, in which chamber the individual liquid components are mixed together. In order to provide a notion of the orders or magnitude, which occur in devices of this type, it can be mentioned that typical conveying capacities are in the range of between 0.1 and 10 ml/min. Accordingly, the volume of the mixing chambers used in this case is within the order of several milliliters.

Known mixing chambers for this application were provided with a stirrer, which consisted of a permanent magnetic member located inside the chamber and of a device located outside the mixing chamber for producing a rotary field. The provision of such a stirrer requires considerable technical resources and in particular both as regards the construction and location of the electromagnet for producing the rotary field, as well as with regard to the necessity of providing a special current supply for this purpose. In this case it should be taken into consideration that the liquids to be mixed may have a very high viscosity and on the other hand, the dimensions of the mixing chamber and of the stirrer located therein are relatively small, so that the production of high moments of rotation is difficult, as the latter could be required for mixing highly viscous liquids. Furthermore, it may be necessary to construct the mixing chamber so that it withstands very high pressures, namely pressures of several hundred Bars. However, the use of such a stirrer precludes ferromagnetic materials for the production of such mixing chambers.

SUMMARY OF THE INVENTION

Accordingly, it is the object of the invention to simplify a mixing chamber of the aforementioned type.

This object is achieved according to the invention due to the fact that the mixing chamber is divided by a fine-pored filter plate into two areas and the inlet pipe is connected to one area and the outlet pipe is connected to the other of these areas.

In the mixing chamber according to the invention, an active stirrer is completely dispensed with, so that the expenditure for such a stirring device is completely eliminated. This also dispenses with limitations as regards the choice of material and in practice an unlimited working life can be expected for a mixing chamber of this type, because moving parts which are subject to wear are completely dispensed with. Furthermore, the mixing chamber according to the invention operates in a troublefree manner with liquids of any viscosity.

With the above-mentioned small quantities to be conveyed and a correspondingly small volume of the mixing chamber, it can be assumed that the pressure of the liquid supplied on the surface of the fine-pored filter plate has the same value at all points, which value corresponds substantially to the static pressure. Consequently, the same flow density prevails over the entire surface of the filter plate. However, since the individual surface elements of the filter plate are at different distances both from the inlet pipe as well as from the outlet pipe, the individual liquid components cover different distances from the inlet pipe to the outlet pipe, which leads to thorough mixing of the portions of the individual liquids supplied one after the other over a period of time.

The mixing chamber can basically have any shape, provided that its cross-section is large with respect to the cross-section of the inlet and outlet pipes, because this necessarily produces the different distances from the openings of these pipes to the individual surface elements of the filter plate. However, a shape of the mixing chamber is preferred, in which at least one of the areas widens out continuously from the opening of the connected pipe towards the filter plate. A shape of this type ensures that the liquid supplied flows through the entire volume of the mixing chamber and there are no stagnant corners where portions of liquid may remain for so long that they falsify the desired mixing proportions, which is to be adjusted on the basis of the supplied quantities of the various liquids.

It is particularly favourable both for mixing of the liquid portions as well as for manufacture if the area widens out in the form of a cone from the opening of the pipe, in which case the opening angle of the cone should amount to more than 90° and preferably should lie within the range of 140° to 160°. The mixing chamber can thus advantageously be constructed symmetrically with respect to the plane defined by the filter plate.

For the manufacture of the filter plate, basically any material is suitable which offers an adequate flow resistance on account of its fine pores, in order to ensure the uniform pressure distribution over the entire surface of the filter plate at least approximately. It is also intended to ensure that the filter plate does not cause any contamination of the liquids passed therethrough. From these points of view, sintered materials seem particularly suitable and for mixing chambers according to the invention, filter plates consisting of steel or glass frits are preferred. In this case, filter plates consisting of a steel frit are used in particular for high pressure mixing chambers and filter plates consisting of a glass frit are used for low pressure mixing chambers. In filter plates of this type, the pore size is in the range of 2 to 50 μm.

A preferred embodiment of a mixing chamber according to the invention consists of two housing parts joined together in the plane of the filter plate, which on their adjoining end faces comprise recesses for receiving the edge of the filter plate and comprise a seal surrounding the filter plate in an annular manner. Particularly with a conical construction of the cavities of the mixing chamber adjoining the filter plate, in a simple manner the two housing parts could be constructed as turned parts and then pressed firmly one against the other by their end faces using suitable tightening screws. In this way, mixing chambers can be manufactured, which can also be used with very high liquid pressures.

With a mixing chamber of this type, it is particularly advantageous if the seal surrounds the filter plate directly and is compressed by the housing both at right angles to the plane of the filter plate and is also pressed radially against the edge of the filter plate. In this embodiment, not only is the provision of a special groove for the sealing ring eliminated, but the same seal brings about not only sealing of the mixing chamber with respect to the outside, but also sealing along the periphery of the filter plate, so that surface-leakage paths along the filter plate are prevented.

In a further embodiment of the invention, at least one of the housing parts may comprise a bore opening into the respective area and at right angles to the plane of the filter plate and a plurality of pipe connections distributed over its periphery, starting from which are radially located bores which open into the aforementioned bore. In this embodiment of the invention, special distributors are thus eliminated and the pipes which supply the liquids to be mixed can be connected directly to the mixing chamber. If, at the outlet side, a distribution of the mixed liquid to several pipes is required, for example in order to produce the connection to the cylinders of a multiple piston pump, then the housing part at the outlet side can also be constructed in the manner described and provided with several pipe connections.

BRIEF DESCRIPTION OF THE DRAWINGS

The invention is described and explained in detail hereafter with reference to the embodiment illustrated in the drawing. The features disclosed in the description and drawings can be used in other embodiments individually or jointly in any combination.

DETAILED DESCRIPTION OF ILLUSTRATIVE EMBODIMENTS

Figure 1:
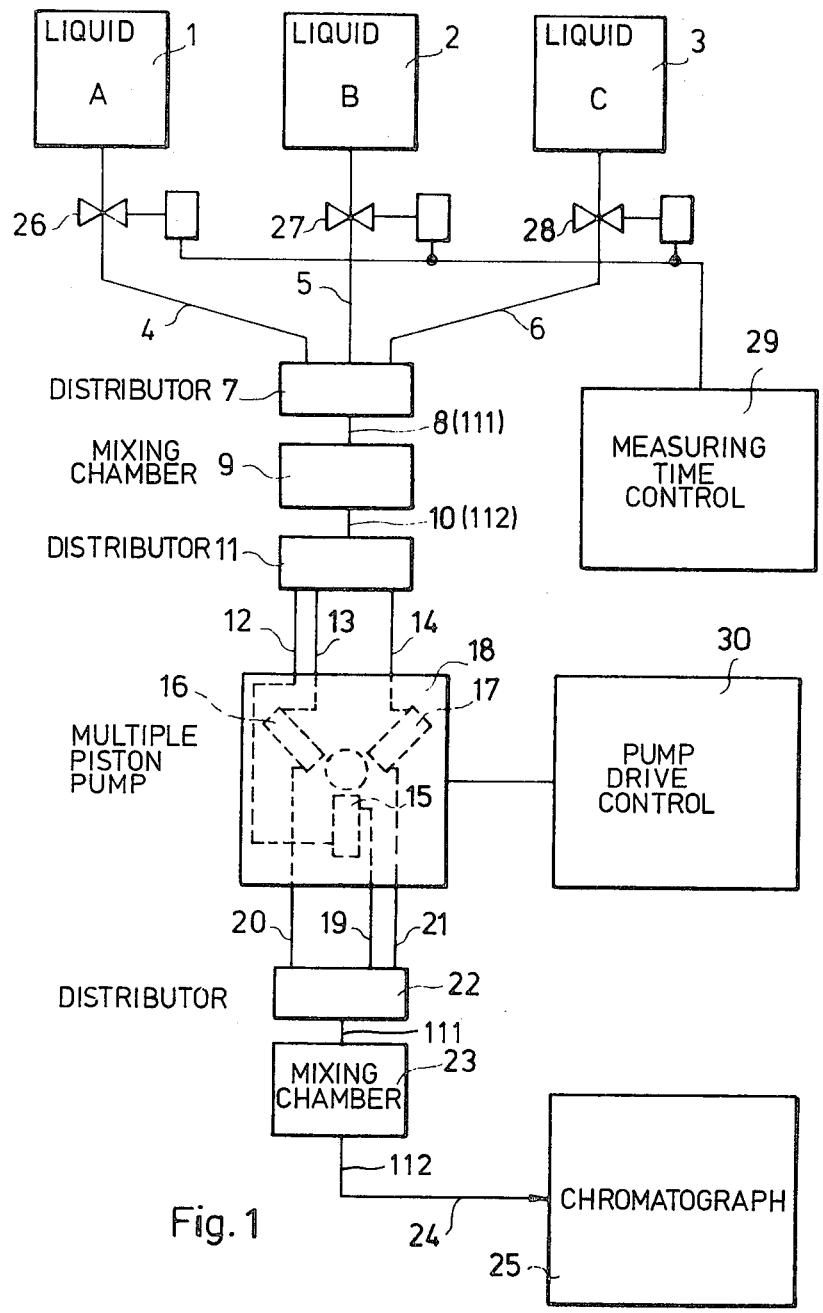
FIG. 1 is a diagrammatic illustration of a device containing mixing chambers for supplying liquid mixtures to a chromatographic analytical instrument.

The device illustrated in FIG. 1 comprises three liquid containers 1,2 and 3, which each contain one liquid A,B or C. The outlet pipe 4,5,6 of these containers 1 to 3 lead to a distributor 7, from which a pipe 8 leads to a mixing chamber 9. The outlet pipe 10 of this mixing chamber leads to a further distributor 11, from which three pipes 12,13,14 lead to the three cylinders 15,16,17 of a multiple piston pump 18. The pipes 19,20,21 leaving the three cylinders 15 to 17 of the multiple piston pump 18 lead to a further distributor 22, to which a further mixing chamber 23 is connected, from which the liquid conveyed is supplied by way of a pipe 24 to a chromatographic analytical instrument 25. Located in each of the outlet pipes 3 to 5 of the containers 1 to 3 is one of three solenoid valves 26 to 28, the opening times of which are determined by a measuring time control 29. The multiple piston pump may be an electronically regulated pump with a constant delivery, as described in the former patent application No. P 30 35 770.1. Accordingly, the pump 18 is connected to a pump drive control 30.

In order to supply a mixture of the liquids A to C present in the containers 1 to 3 to the chromatographic analytical instrument, the solenoid valves 26 to 28 are opened alternately, individually one after the other by means of the measuring time control 29, so that one of the three liquids passes respectively by way of the distributor 7 into the mixing chamber 9. As a result of the suction action of the pump 18, assuming a constant suction speed of the multiple piston pump, the quantity of liquid conveyed is strictly proportional to the opening time of the valves 26 to 28, so that also the quantities of the three liquids which are supplied to the mixing chamber 9 are strictly proportional to the opening times of the individual valves. It is the function of the mixing chamber 9 to produce a homogeneous mixture from the portions of liquid supplied in succession over a period of time. The distributor 11 located after the mixing chamber 9 is necessary in order to supply the liquid mixture to the three cylinders of the multiple piston pump used in this case. An amalgamation of the quantities of liquid supplied by the three cylinders of the pump is likewise necessary at the outlet of the pump 18, for which purpose the distributor 22 is provided. Since in this case the three quantities of liquid are once more supplied in an alternating manner over a period of time, possibly even with a certain overlap, the additional mixing chamber 23 can be incorporated at this point in order to provide further mixing of the quantities of liquid supplied by the three cylinders. However, in principle, one of the two mixing chambers 9 and 23 is sufficient. When using only one mixing chamber, the mixing chamber 23 at the high pressure side is preferably used, because due to the cylinders of the pump 18 operating with a certain time lag one with respect to the other, a certain amount of pre-mixing of the liquids conveyed is achieved in the distributor 22.

Figure 2:
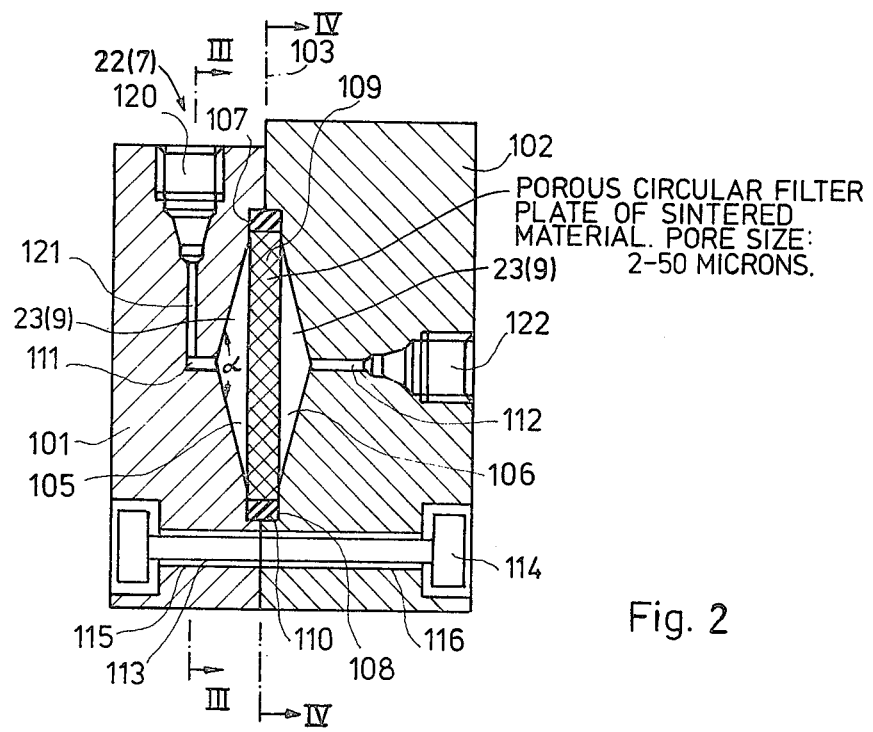
FIG. 2 is a cross-section through one of the mixing chambers used in the device according to FIG. 1
Figure 3:
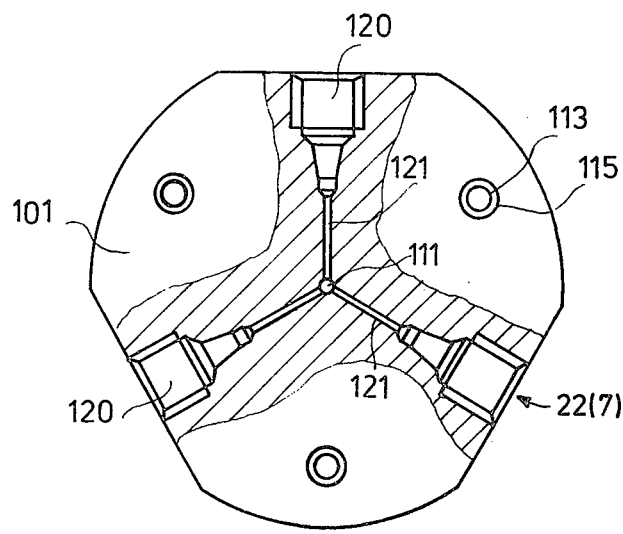
FIG. 3 is a section on line III—III through the mixing chamber according to FIG. 2.
Figure 4:
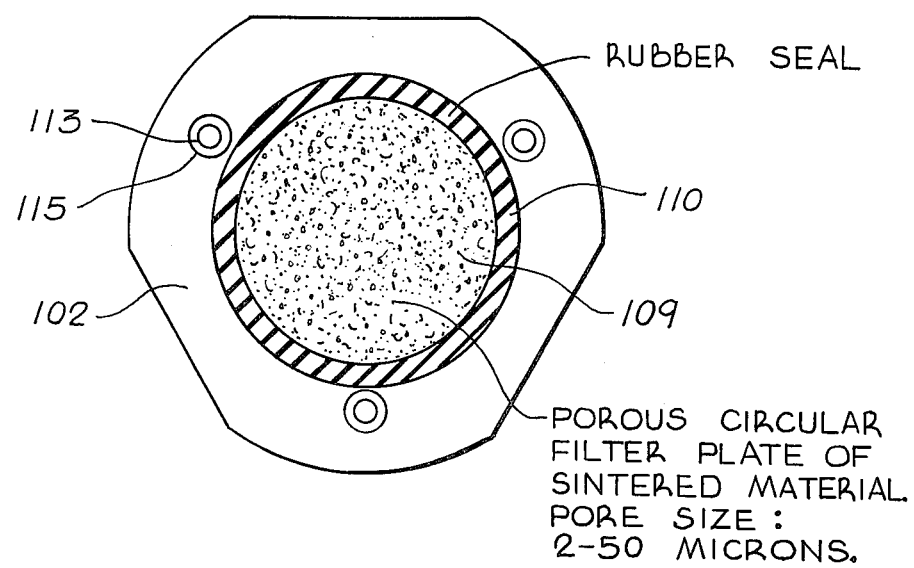
FIG. 4 is a section on the line IV—IV in FIG. 2.

FIGS. 2 and 3 show one embodiment of a mixing chamber according to the invention, which is particularly suitable as a high pressure mixing chamber 23. This mixing chamber consists of two housing parts 101 and 102, which bear one against the other by their end faces located in a common plane 103. Located in these end faces are recesses, which form areas 105 and 106 located on both sides of the plane 103 and furthermore comprise sections 107, 108 for receiving the edge of a filter plate 109 and a seal 110. Respectively connected to the areas 105 and 106 is an inlet pipe 111 and an outlet pipe 112, which are formed by a bore at right angles to the plane 103 in each of the two housing parts 101 and 102. The areas 105 and 106 have a conical construction and the pipes 111 and 112 open respectively into the tip of the cone so that the areas 105 and 106 widen out continuously from the opening of the pipes 111 and 112 in the direction of the filter plate 109. The two housing parts 101 and 102 are held together by screw bolts 113 and nuts 114, which are inserted in the bores 115,116 provided for this in the housing parts 101,102. The dimensions of the seal 110 are such that its thickness at right angles to the plane 103 is somewhat greater than the inside width in the recesses provided for receiving it, so that it is compressed at right angles to the plane 103 when the parts 101 and 102 are screwed together. Before being compressed, its outer diameter corresponds to the outer diameter of the recesses, so that at the time of compression, the seal is pressed against the periphery of the filter plate 109 and the seal 110 not only seals the housing parts with respect to each other but also seals the filter plate 109 with respect to the housing in a troublefree manner.

In the embodiment illustrated, the housing part 101 comprising the inlet pipe 111 contains three radial pipe connections 120, which are connected by way of radially located bores 121 to the bore 111 at right angles to the plane 103 and opening into the space 105. The other housing part 102 comprises only one pipe connection 122, which is arranged as an extension of the bore 112 perpendicular to the plane 103. Other embodiments of the invention could consist of two identical housing parts 101 or two identical housing parts 102. In the latter case, at least the inlet side of the mixing chamber would have to be preceded by a special distributor, whereas the housing part 101 comprises a distributor with three connections.

The embodiment of a mixing chamber illustrated in FIGS. 2 and 3 is particularly suitable as the mixing chamber 23 on the high pressure side of the device according to FIG. 1, because it comprises a distributor with three inlets and a single outlet, to which the analytical instrument 25 can be connected directly. Since pressures of several hundred Bars occur in devices of this type, it is appropriate to manufacture the housing parts 101 and 102 from stainless steel. Although the pressure differences occurring at the filter plate 109 are not excessively great, it nevertheless seems advisable to use a material which is able to tolerate even greater differences between the pressures acting on its surfaces. A sintered material in the form of a steel frit has proved particularly suitable. The pore size of such a material is within the order of magnitude of 5 $\mu$m. In an embodiment which has been put into operation, the filter plate has a diameter of approximately 20 mm and a thickness of approximately 2 mm. A suitable material for the sealing ring 108 is a fluorinated polyethylene. The opening angle $\alpha$ of the conical areas amounts to 152°. With this angle, the height of the conical area amounts to approximately 10 mm, so that the distances from the inlet pipe to the centre or to the edge of the filter plate are in a ratio of approximately 1:2. The same is true for the outlet side of the mixing chamber.

Since, in the arrangement according to FIG. 1, a distributor with three connections is required for the mixing chamber 9 both at the inlet side as well as at the outlet side, in this case the use of a mixing chamber is recommended composed of two identical housing parts 101, which each comprise a distributor with three connections. Since the mixing chamber 9 is located on the low pressure side of the pump 18, the housing parts may consist of a material which is less resistant to pressure, for example of a synthetic material which is neutral with respect to solvents. Halogenated polyethylenes are particularly suitable. The material used for the seal 110 must naturally be more elastic than the housing material. A glass frit could be used in this case as the filter plate. Suitable glass frits can be obtained with a pore diameter of approximately 30 $\mu$m.

The variations dealt with herebefore show that the invention is not limited to the embodiment illustrated. It is only critical for the invention that the mixing chamber is divided by a filter plate into two areas and that the distance covered by the liquid from the inlet pipe and/or outlet pipe to the various points on the surface of the filter plate varies. In this case it may be appropriate if the individual areas have an asymmetrical construction, for example because with the same plate dimensions and the same height of the area, shifting the pipes to one edge of the filter plate results in a greater ratio of path lengths and thus better mixing of the liquids. It could also possibly be appropriate to construct the inlet area and outlet area in a different manner. Finally, it is solely important for the filter plate that it forms a baffle member, on the surface of which the most uniform possible pressure builds up, so that the flow density is identical over the entire surface of the filter plate and on account of the varying distances which the portions of the liquid associated with the individual surface elements of the filter plate must cover, thorough mixing of the liquids passed through the mixing chamber results. Therefore, in addition to sintered materials, laminated lattice arrangements, fibrous materials etc., are also suitable, provided that it is ensured that they do not contaminate the liquids passing therethrough and do not seggregate particles which could block the very thin feed pipes in the application described.

We claim:

1. Liquid-mixing apparatus for producing a substantially homogeneous mixture of a plurality of liquids for supplying such mixture to a liquid chromatograph, said apparatus comprising a plurality of liquid supply means for supplying a plurality of liquids, housing means having inlet means and outlet means, liquid measuring time control means connected between said supply means and said inlet means for supplying the liquids in small measured quantities one after the other in succession to said inlet means for repetitive time cycles covering successive periods of time, said housing means having a single mixing chamber therein, and a single fine-pored filter plate disposed in said mixing chamber and dividing said mixing chamber into a single inlet portion and a single outlet portion, said inlet portion of said mixing chamber having a single inlet opening connected to said inlet means, said outlet portion of said mixing chamber having a single outlet opening connected to said outlet means, said filter plate having a small pore size in the range of two to fifty microns, said inlet portion of said mixing chamber widening out between said inlet opening and said filter plate at an opening angle more than 90°, said outlet portion of said mixing chamber widening out between said outlet opening and said filter plate at an opening angle more than 90°, said filter plate having a diameter substantially greater than the diameter of said inlet opening whereby there is a correspondingly great variation between the maximum and minimum path length between said inlet opening and the various portions of said filter plate, said filter plate having a substantially greater diameter than the diameter of said outlet opening whereby there is a correspondingly great variation between the maximum and minimum path length between various portions of said filter plate and said outlet opening, said fine-pored filter plate forming a buffer member having an inlet side surface on which substantially uniform liquid pressure builds up and over which surface the liquid flow density is substantially identical, said great variations in path length and the small pore size of said filter plate causing substantially homogeneous mixing of the small successive quantities of the liquids supplied to said inlet opening.

2. Liquid-mixing apparatus according to claim 1, in which each of said inlet and outlet portions of said mixing chamber widens out continuously in substantially the shape of a cone.

3. Liquid-mixing apparatus according to claim 1, in which said opening angle ranges from 140° to 160° to provide great variations in said path length.

4. Liquid-mixing apparatus according to claim 1, said housing means comprising two housing parts joined together substantially in the plane of said filter plate, said housing parts having adjoining end faces with recesses therein for receiving the peripheral portion of said filter plate, and an annular seal surrounding said peripheral portion of said filter plate and received in said recesses, said seal being compressed against said peripheral portion of said filter plate and also against said housing parts to prevent leakage around said filter plate and out of said mixing chamber.

5. A liquid-mixing device for producing a substantially homogeneous mixture of a plurality of liquids supplied in a small measured quantities one after the other in repetitive cycles covering successive periods of time and for supplying said mixture to a liquid chromatograph, said device comprising
housing means having a single mixing chamber therein, and
a single fine-pored filter plate disposed in said mixing chamber and dividing said mixing chamber into a single inlet portion and a single outlet portion,
said housing means having a single inlet opening extending into said inlet portion for receiving the successive small measured quantities of the liquids,
said housing means having a single outlet opening extending out of said outlet portion for discharging the mixture of the liquid,
said filter plate consisting of a sintered material having a small pore size in the range of two to fifty microns,
said inlet portion of said mixing chamber widening out continuously from said inlet opening towards said filter plate at an opening angle more than 90°,
said outlet portion of said mixing chamber widening out continuously from said outlet opening towards said filter plate at an opening angle more than 90°,
said filter plate having a substantially greater diameter than said inlet opening and thereby producing a correspondingly great variation between the maximum and minimum path length between said inlet opening and the various portions of said filter plate,
said filter plate having a substantially greater diameter than said outlet opening and thereby producing a correspondingly great variation between the maximum and minimum path length between various portions of said filter plate and said outlet opening,
said fine-pored filter plate forming a buffer member having an inlet side surface on which substantially uniform liquid pressure builds up and over which surface the liquid flow density is substantially identical,
said wide variations in said path length and said small pore size of said filter plate being effective to produce substantially homogeneous mixing of the small measured quantities of said liquids received through said inlet opening.

6. A liquid-mixing device according to claim 5, in which said opening angle of said inlet and outlet portions of said mixing chamber ranges from 140° to 160°.

7. A liquid-mixing device according to claim 5, said housing means comprising two housing parts joined together in substantially the plane of said filter plate, said housing parts having adjoining end faces with recesses therein for receiving the peripheral portion of said filter plate, and an annular seal surrounding said peripheral portion of said filter plate and received in said recesses, said seal being compressed against said peripheral portion of said filter plate and also against said two housing parts to prevent any leakage past said filter plate or out of said mixing chamber.

8. Liquid-mixing apparatus for producing a substantially homogeneous mixture of a plurality of liquids for supplying such mixture to a liquid chromatograph, said apparatus comprising
a plurality of liquid supply means for supplying a plurality of liquids,
housing means having inlet means and outlet means,
liquid measuring time control means connected between said supply means and said inlet means for supplying the liquids in small measured quantities one after the other in succession to said inlet means for repetitive time cycles covering successive periods of time,
said housing means having a single mixing chamber therein,
and a single fine-pored filter plate disposed in said mixing chamber and dividing said mixing chamber into a single inlet portion and a single outlet portion,
said inlet portion of said mixing chamber having a single inlet opening connected to said inlet means,
said outlet portion of said mixing chamber having a single outlet opening connected to said outlet means,
said filter plate having a small pore size in the range of two to fifty microns,
said inlet portion of said mixing chamber widening out between said inlet opening and said filter plate at an opening angle more than 90°,
said outlet portion of said mixing chamber widening out between said outlet opening and said filter plate at an opening angle more than 90°,
said filter plate having a diameter substantially greater than the diameter of said inlet opening whereby there is a correspondingly great variation between the maximum and minimum path length between said inlet opening and the various portions of said filter plate,
said filter plate having a substantially greater diameter than the diameter of said outlet opening whereby there is a correspondingly great variation between the maximum and minimum path length between various portions of said filter plate and said outlet opening,
said fine-pored filter plate forming a buffer member having an inlet side surface on which substantially uniform liquid pressure builds up and over which surface the liquid flow density is substantially identical,
said great variations in path length and the small pore size of said filter plate causing substantially homogeneous mixing of the small successive quantities of the liquids supplied to said inlet opening,
said filter plate consisting of a sintered material.

9. Liquid-mixing apparatus according to claim 8, in which said filter plate consists of a sintered material made of steel frit.

10. Liquid-mixing apparatus according to claim 8, in which said filter plate consists of a sintered material made of glass frit.

* * * * *